United States Patent
Choi et al.

(10) Patent No.: US 9,433,931 B2
(45) Date of Patent: Sep. 6, 2016

(54) HIGH PERFORMANCE POLYOXOMETAL CATALYST AND METHOD FOR PRODUCING THE SAME

(71) Applicant: LG CHEM, LTD., Seoul (KR)

(72) Inventors: Byung Yul Choi, Daejeon (KR); Hyun Jong Shin, Daejeon (KR); Ju Yeon Park, Daejeon (KR); Young Hyun Choi, Daejeon (KR); Duk Ki Kim, Daejeon (KR); Hyun Sub Lim, Daejeon (KR)

(73) Assignee: LG CHEM, LTD., Seoul (KR)

( * ) Notice: Subject to any disclaimer, the term of this patent is extended or adjusted under 35 U.S.C. 154(b) by 0 days.

(21) Appl. No.: 14/890,545

(22) PCT Filed: Jul. 6, 2015

(86) PCT No.: PCT/KR2015/006907
§ 371 (c)(1),
(2) Date: Nov. 11, 2015

(87) PCT Pub. No.: WO2016/006883
PCT Pub. Date: Jan. 14, 2016

(65) Prior Publication Data
US 2016/0175818 A1    Jun. 23, 2016

(30) Foreign Application Priority Data

Jul. 9, 2014   (KR) .................. 10-2014-0085819
Jun. 25, 2015  (KR) .................. 10-2015-0090217

(51) Int. Cl.
*B01J 37/04*   (2006.01)
*C07C 51/235*  (2006.01)
*B01J 23/889*  (2006.01)
*B01J 23/888*  (2006.01)
*B01J 37/02*   (2006.01)
*B01J 37/08*   (2006.01)

(52) U.S. Cl.
CPC ......... *B01J 23/8892* (2013.01); *B01J 23/8885* (2013.01); *B01J 37/0215* (2013.01); *B01J 37/0236* (2013.01); *B01J 37/04* (2013.01); *B01J 37/08* (2013.01); *C07C 51/235* (2013.01)

(58) Field of Classification Search
CPC .. B01J 23/8892; B01J 23/8885; B01J 37/04; B01J 37/0215; B01J 37/0236; B01J 37/08; C07C 51/235
See application file for complete search history.

(56) References Cited

U.S. PATENT DOCUMENTS

| | | | |
|---|---|---|---|
| 4,634,502 A | 1/1987 | Callahan et al. | |
| 4,898,989 A | 2/1990 | Ellis, Jr. et al. | |
| 5,990,348 A | 11/1999 | Lyons et al. | |
| 6,387,841 B1* | 5/2002 | Devlin | B01J 23/002 502/208 |
| 6,914,029 B2* | 7/2005 | Davis | B01J 27/186 502/150 |
| 2012/0197033 A1* | 8/2012 | Neumann | B01J 23/6527 556/136 |

FOREIGN PATENT DOCUMENTS

| | | |
|---|---|---|
| JP | 2008-155126 A | 7/2008 |
| KR | 2001-0067093 A | 7/2001 |
| KR | 10-2005-0043737 A | 5/2005 |
| KR | 10-0714606 B1 | 5/2007 |

* cited by examiner

*Primary Examiner* — Shailendra Kumar
(74) *Attorney, Agent, or Firm* — Dentons US LLP

(57) ABSTRACT

Disclosed are a high-performance polyoxometalate catalyst and a method of preparing the same. More particularly, disclosed are a high-performance polyoxometalate catalyst which may enhance activity and selectivity by controlling the content of vanadium, etc. exhibits superior reproducibility, and may produce unsaturated carboxylic acid with high yield and long lifespan from unsaturated aldehyde, and a method of preparing the same.

20 Claims, No Drawings

HIGH PERFORMANCE POLYOXOMETAL CATALYST AND METHOD FOR PRODUCING THE SAME

CROSS-REFERENCE TO RELATED APPLICATION(S)

This application is a National Stage Entry of International Application No. PCT/KR2015/006907, filed Jul. 6, 2015, which application claims the benefit and priority to Korean Patent Application No. 10-2014-0085819, filed Jul. 9, 2014, and Korean Patent Application No. 10-2015-0090217, filed Jun. 25, 2015, in the Korean Intellectual Property Office, the disclosures of which are incorporated herein by reference.

TECHNICAL FIELD

The present invention relates to a polyoxometalate catalyst and a method of preparing the same. More particularly, the present invention relates to a catalyst used to prepare unsaturated carboxylic acid from unsaturated aldehyde gas through partial vapor-phase oxidation in a shell-and-tube heat exchanger, and a method of preparing the same.

BACKGROUND ART

Processes of producing unsaturated fatty acids from olefins through unsaturated aldehyde correspond to representative catalytic vapor phase oxidation.

In partial oxidation of olefins, molybdenum oxides, bismuth oxides, and transition metal oxides are used to prepare catalysts. As representative processes, there are a process of preparing (meth)acrylic acid through (meth)acrolein by oxidizing propylene or isobutylene, a process of preparing phthalic anhydride by oxidizing naphthalene or ortho-xylene, or a process of preparing maleic anhydride by partially oxidizing benzene, butylene or butadiene.

In the first step, oxygen, propylene or isobutylene is oxidized by dilute inactive gas, vapor and a predetermined amount of catalyst, mainly preparing (meth)acrolein. In the second step, the (meth)acrolein is oxidized by oxygen, dilute inactive gas, vapor and a predetermined amount of catalyst, thereby preparing the (meth)acrylic acid. Devices performing such processes may be provided such that both steps are performed in one device or in respective devices.

The (meth)acrylic acid is mainly used to prepare (meth)acrylate used as coating materials such as paint, textile auxiliaries, paper, etc. by reacting with alcohol. In addition, high-purity (meth)acrylic acid is used as a raw material of high-hygroscopicity resins, demand for which is rapidly increasing.

In general, metal oxide catalysts are prepared through co-precipitation, hydrothermal synthesis, sol-gel synthesis, physical mixing, etc. The metal oxide catalysts are precipitated into a polyanion, metal oxide or metal hydroxylate form in the reaction processes, and physical characteristics and morphologies of the precipitates depend upon the pH or concentration of an aqueous solution, reaction temperature or aging time, thereby affecting a physical state, particle sizes and crystalline structure.

Examples of ligands that are bonded to oxoanions and transition metal precursors used in catalysts for preparing unsaturated fatty acids include —NH$_4$, —NH$_2$, —NO$_x$, —Cl, —F, —N, —OH (hydroxyl), —SO$_x$, —CO, —COO, —C$_n$H$_m$O$_x$, alkoxide (O-metal), etc. Such ligands may be utilized as an ingredient for controlling catalytic activities by changing physicochemical characteristics of catalysts according to proper control methods as an essential ingredient upon dissolution or purification of metal oxides.

Japanese Patent No. 4295521 as a related art introduces a catalyst preparation technology wherein a catalyst is prepared by powder-coating and firing a bulk carrier. This technology produces an acrylic acid catalyst wherein a reduction ratio of a dry matter is 5 to 40% by mass at a 300° C. atmosphere as a catalyst-drying temperature. Such a preparation method has a relatively high drying temperature and thus change in a catalyst structure is caused, thereby disadvantageously affecting catalytic performance and thus tending to exhibit a low transition rate.

In addition, Korean Patent No. 10-0746971 introduces a catalyst wherein the catalyst includes molybdenum and vanadium, the content of catalyst poison measured by ion chromatography is 10 to 100 ppb, at least one volatile catalyst poison ingredient is additionally included, and acrylic acid is generated through vapor-phase contact oxidation of oxygen molecules and acrolein, and an acrylic acid preparation method including performing catalytic vapor phase oxidation of oxygen molecules and acrolein using the catalyst.

The catalyst is prepared through addition of aqueous ammonia as a catalyst poison ingredient, thereby lowering hot spot temperature and suppressing reaction efficiency decrease accompanied with degradation. Accordingly, an acrolein transition rate may be stably maintained for a long time. However, if a reducing material such as ammonia is present in a catalyst, the material functions as a catalyst poison, thus greatly increasing reaction temperature and activating the catalyst after extended use. Accordingly, a reducing material may be used as a catalyst poison for controlling catalytic activity, but there are considerable difficulties in performing quantitative control during a catalyst preparation process.

In addition, although inorganic salts present in catalyst precursors should be treated such that the amount thereof is decreased during a catalyst preparation process, a reducing material removal process is additionally required due to further addition of inorganic salts. Accordingly, there is a need for technology being simple and having superior reproducibility, which may sublimate, during catalyst calcination, ligands included in a catalyst.

DISCLOSURE

Technical Problem

Therefore, the present invention has been made in view of the above problems, and it is one object of the present invention to provide a high-performance polyoxometalate catalyst which may control activity and selectivity, has superior reproducibility, and may produce unsaturated carboxylic acid with high yield and long lifespan from unsaturated aldehyde, and a method of preparing the same.

The above and other objects can be accomplished by the present invention described below.

Technical Solution

In accordance with one aspect of the present invention, provided is a polyoxometalate catalyst comprising a metal oxide represented by Formula 1 below:

$$Mo_aA_bV_cB_dC_eD_fO_g \qquad \text{[Formula 1]}$$

wherein A is at least one element selected from W and Cr, B is at least one element selected from the group consisting of P, As, B, Sb, Ce, Pb, Mn, Nb and Te, C is at least one element selected from the group consisting of Si, Al, Zr, Rh, Cu, Ni, Ti, Ag, Fe, Co and Sn, D is at least one element selected from the group consisting of Na, K, Li, Rb, Cs, Ta, Ca, Mg, Sr and Ba, and a, b, c, d, e, f and g denote an atomic ratio of each element, but, when a=12, b is 0.01 to 15, c is 0.01 to 15, d is 0 to 20, e is 0 to 20, f is 0 to 20, and g is determined according to an oxidation state of each of the ingredients, wherein, in the vanadium (V), a mole ratio of $V^{4+}$ relative to a sum of $V^{4+}$ and $V^{5+}$ is 0.47 to 1.

In an embodiment, each of d, e and f may be 0.01 to 20.

In an embodiment, a mole ratio of V to A (V/A) may be 0.01 to 10.

In an embodiment, the polyoxometalate catalyst may include an inactive carrier as a support of the metal oxide.

In an embodiment, a coating amount of the metal oxide coated on the inactive carrier may be 30 to 80% by weight.

In an embodiment, the polyoxometalate catalyst may be a partial vapor-phase oxidation catalyst generating carboxylic acid from unsaturated aldehyde.

In accordance with another aspect of the present invention, provided is a method of preparing a polyoxometalate catalyst, the method comprising: A) preparing a suspension including metal precursors in order to produce a metal oxide represented by Formula 1 and, as needed, adjusting pH to 0 to 7.5 through addition of acid, and then forming polyoxometalate by increasing viscosity using a homogenizer; B) preparing a support material by coating an inactive carrier with 20 to 50% by weight of the polyoxometalate; C) obtaining a support material having a ligand sublimation rate of 0% or more calculated according to Equation 1 below by drying the support material; and D) obtaining a polyoxometalate catalyst by firing the dried support material:

Ligand sublimation rate (%)=(Mass of sublimated ligand/mass of ligand before sublimation)×100.  [Equation 1]

In an embodiment, the viscosity of the polyoxometalate of step (A) may be 1,000 to 15,000 cP or 3,000 to 8,000 cP.

In an embodiment, the polyoxometalate of step (A) may be ground after drying, or filtrating and drying.

In an embodiment, the coating of step (B) may be performed by spraying the polyoxometalate, or the polyoxometalate with water to the inactive carrier.

In an embodiment the suspension of step (A) may be prepared by inputting an aqueous vanadium solution treated with acid and metal to a suspension comprising all or a portion of metal precursors except for a vanadium precursor.

In an embodiment, the acid may be inorganic acid.

In an embodiment, the metal may be one or more of Group I, II and XII to XVI metals.

In another embodiment, the metal may be a metal which may reduce $V^{5+}$ to $V^{4+}$ in the presence of an acid catalyst.

In an embodiment, a ligand of the metal precursor may be one or more selected from $-NH_4$, $-NH_2$, $-NOx$ (x being an integer of 1 to 4), $-Cl$, $-F$, $-N$, $-OH$, $-SOx$ (x being an integer of 1 to 4), $-CO$, $-COO$, $-SCN$, $-CN$, $-NCS$, $-ONO$, $-NC$, $-C_nH_mO_x$ (n being an integer of 1 to 20, m being an integer of 1 to 40, and x being an integer of 1 to 10) and $C_1$ to $C_{20}$ alkoxide.

In an embodiment, in step (A), a concentration of the suspension may be 25 to 45% by weight or 30 to 40% by weight.

In an embodiment, the drying of step (C) may be hot air drying.

In an embodiment, the coating of step (B) may be performed by repeatedly coating and drying the polyoxometalate on the inactive carrier once or more.

In an embodiment, the drying of step (C) may be performed at 100 to 230° C.

In an embodiment, in step (A), the polyoxometalate may be formed by increasing a viscosity of the suspension by means of a homogenizer at 25 to 50° C.

In an embodiment, the firing of step (D) may be performed at 350 to 500° C. for 1 to 10 hr.

In accordance with yet another aspect of the present invention, provided is a method of preparing unsaturated carboxylic acid wherein partial vapor-phase oxidation to produce unsaturated carboxylic acid from unsaturated aldehyde gas is preformed in a fixed-bed catalyst reactor filled with the polyoxometalate catalyst according to claims 1 at 240 to 450° C. under 0.1 to 10 atm.

In an embodiment, the fixed-bed catalyst reactor may be a shell-and-tube heat exchanger.

Advantageous Effects

As apparent from the fore-going, the present invention advantageously provides a high-performance polyoxometalate catalyst which may enhance activity and selectivity by controlling the content of vanadium, etc. exhibits superior reproducibility, and may produce unsaturated carboxylic acid with high yield and long lifespan from unsaturated aldehyde, and a method of preparing the same.

BEST MODE

Hereinafter, the present invention is described in more detail.

A polyoxometalate catalyst according to the present invention includes a metal oxide represented by Formula 1 below:

   [Formula 1]

wherein A is at least one element selected from W and Cr, B is at least one element selected from the group consisting of P, As, B, Sb, Ce, Pb, Mn, Nb and Te, C is at least one element selected from the group consisting of Si, Al, Zr, Rh, Cu, Ni, Ti, Ag, Fe, Co and Sn, D is at least one element selected from the group consisting of Na, K, Li, Rb, Cs, Ta, Ca, Mg, Sr and Ba, and a, b, c, d, e, f and g denote an atomic ratio of each element, but, when a=12, b is 0.01 to 15, c is 0.01 to 15, d is 0 to 20, e is 0 to 20, f is 0 to 20, and g is determined according to an oxidation state of each of the ingredients, wherein, in the vanadium (V), a mole ratio of $V^{4+}$ relative to a sum of $V^{4+}$ and $V^{5+}$ is 0.47 to 1.

In the present disclosure, the expression "polyoxometalate" means general polyoxometalate unless otherwise specified.

In the present disclosure, the expression "ligand" means an anion group, which is bonded to metallic cations in a metal precursor, and a general ligand, unless otherwise specified.

In an embodiment, in the metal oxide, a mole ratio of $V^{4+}$ to the total content of vanadium (V) ($V^{4+}/(V^{4+}+V^{5+})$) is 0.47 to 0.8, 0.5 to 0.8, or 0.52 to 0.72. Within this range, activity and selectivity of the catalyst are enhanced, superior reproducibility is exhibited, and unsaturated carboxylic acid having high yield and long lifespan may be produced.

In an embodiment, each of d, e and f may be 0.01 to 20, or 0.5 to 3. Within this range, oxidation of vanadium is affected and, thus, the catalyst exhibits superior activity and selectivity. In particular, tungsten (W) functions as a structural promoter in the catalyst, thereby enhancing catalytic activity by increasing the amount of $V^{4+}$ in the catalyst.

In an embodiment, b may be 0.1 to 10, 1.0 to 6.0, or 1.5 to 5.0. Within this range, activity, selectivity and lifespan of the catalyst are greatly enhanced.

In an embodiment, c may be 0.5 to 10, 1.0 to 5.0, or 2.0 to 3.0. Within this range, activity, selectivity and lifespan of the catalyst are greatly enhanced.

In an embodiment, d, e and f may be respectively 0.01 to 20, or 0.05 to 10.

In another embodiment, d may be 0.01 to 0.5, 0.05 to 0.4, or 0.1 to 0.3, e may be 0.1 to 8.0, 0.5 to 7.0, or 1.0 to 5.5, and f may be 0.1 to 5.0, 0.5 to 2, or 0.8 to 1.3. Within this range, the catalyst exhibits superior activity and selectivity.

In an embodiment, A may be W, and B may be Nb, Mn or a mixture thereof. In an embodiment, C is one or more selected from the group consisting of Cu, Fe and Co, and D may be Sr. In this case, activity and selectivity of the catalyst are enhanced, superior reproducibility is exhibited, and unsaturated carboxylic acid having high yield and long lifespan may be produced.

In an embodiment, the polyoxometalate catalyst may include an inactive carrier as a support of the metal oxide.

In an embodiment, the inactive carrier may be one or more selected from the group consisting of porous aluminosilicate, silicone carbide alumina and silica.

In an embodiment, a coating amount of metal oxide to the inactive carrier may be 30 to 80% by weight, 40 to 70% by weight, or 50 to 60% by weight. Within this range, the catalyst exhibits superior activity and selectivity.

In an embodiment, the polyoxometalate catalyst may be a partial vapor-phase oxidation catalyst generating carboxylic acid from unsaturated aldehyde.

A method of preparing a polyoxometalate catalyst according to the present invention includes A) preparing a suspension including metal precursors in order to produce a metal oxide represented by Formula 1 and, as needed, adjusting pH to 0 to 7.5 through addition of acid, and then forming polyoxometalate by increasing viscosity using a homogenizer; B) preparing a support material by coating an inactive carrier with the polyoxometalate; C) obtaining a support material having a ligand sublimation rate of 0% or more calculated according to Equation 1 below by drying the support material; and D) obtaining a polyoxometalate catalyst by firing the dried support material:

$$\text{Ligand sublimation rate (\%)} = (\text{Mass of sublimated ligand/mass of ligand before sublimation}) \times 100. \quad [\text{Equation 1}]$$

In an embodiment, the viscosity of the polyoxometalate of step (A) may be 1,000 to 15,000 cP or 3,000 to 8,000 cP. Within this range, the catalyst exhibits superior activity and selectivity.

In an embodiment, in step (A), pH may be adjusted to 3 to 5, particularly 4 to 5. Within this range, the catalyst exhibits superior activity, selectivity and lifespan, and drying time and drying temperature are decreased.

In an embodiment, the polyoxometalate of step (A) may be ground after drying, or filtrating and drying.

In an embodiment, the filtration may be a process to remove inorganic salts from slurry-type polyoxometalate by means of a filter and/or a filter press.

In an embodiment, in step (A), the preparing of the suspension may include reducing a vanadium ion, $V^{5+}$, to $V^{4+}$ using acid and metal. In this case, activity, selectivity and lifespan of the catalyst are enhanced.

In another embodiment, in step (A), the preparing of the suspension may include inputting an aqueous vanadium solution treated with acid and metal to a suspension comprising all or a portion of metal precursors except for a vanadium precursor. In this case, activity, selectivity and lifespan of the catalyst are greatly enhanced.

In an embodiment, the acid may be an inorganic acid or an aqueous inorganic acid solution, particularly an aqueous inorganic acid solution having a mass percent concentration of 20% or less, or 5 to 20%.

In an embodiment, the amount of the acid may be 10 to 200 parts by weight, or 100 to 150 parts by weight based on 100 parts by weight of the vanadium precursor.

In an embodiment, the metal may be one or more of Group I, II and XII to XVI metals.

In another embodiment, the metal may be a metal which may reduce $V^{5+}$ to $V^{4+}$ in the presence of an acid catalyst.

In an embodiment, the amount of the metal may be 1 to 40 parts by weight, 10 to 30 parts by weight, or 15 to 25 parts by weight based on 100 parts by weight of the vanadium precursor.

In an embodiment, a ligand of the metal precursor may be one or more selected from —$NH_4$, —$NH_2$, —NOx (x being an integer of 1 to 3), —Cl, —F, —N, —OH, —SOx (x is an integer of 3 to 4), —CO, —COO, —SCN, —CN, —NCS, —ONO, —NC, —$C_nH_mO_x$ (n being an integer of 1 to 20, m being an integer of 1 to 40, and x being an integer of 1 to 10) and $C_1$ to $C_{20}$ alkoxide. In this case, oxidation states and morphologies of the transition metal and the transition metal oxide are affected, thereby enhancing activity and selectivity of the catalyst.

In an embodiment, in step (A), a concentration of the suspension may be 25 to 45% by weight or 30 to 40% by weight. Within this range, the catalyst exhibits superior activity and selectivity.

In an embodiment, in step (A), polyoxometalate may be formed by increasing the viscosity of the suspension by means of a homogenizer at 25 to 50° C., particularly at 20 to 40° C. Within this range, the catalyst exhibits superior activity and selectivity. Here, the polyoxometalate may correspond to a precursor of the polyoxometalate catalyst according to the present disclosure.

In an embodiment, the viscosity of the polyoxometalate may be 1,000 to 15,000 cP or 3,000 to 8,000 cP. Within this range, the catalyst exhibits superior activity and selectivity.

In an embodiment, the polyoxometalate of step (A) may additionally comprise a surfactant. In this case, layer separation of a co-precipitation solution may be decreased.

In an embodiment, the surfactant may be a non-ionic surfactant or a neutral surfactant.

In an embodiment, the non-ionic surfactant may be $CH_3(CH_2)_{15}(EO)nOH$ (n being an integer of 2 to 20).

In an embodiment, the neutral surfactant may be $CH_3(CH_2)n-1NH_2$ (n being an integer of 12 to 16).

In an embodiment, the surfactant may be included in an amount of 0.1% by weight or less, 0.001 to 0.1% by weight, or 0.01 to 0.05% by weight with respect to the total weight of slurry solution. Within this range, layer separation of a co-precipitation solution is decreased.

In step (A), the method of forming polyoxometalate may be a method conventionally used to form polyoxometalate such as hydrothermal reaction, co-precipitation, etc., unless specified otherwise.

In an embodiment, the coating of step (B) may be performed by spraying the polyoxometalate, or the polyoxometalate with water to the inactive carrier.

In an embodiment, through the spraying, slurry-type polyoxometalate, which is not subjected to filtration or drying, may be sprayed and thus coated on the inactive carrier by means of a nozzle.

In an embodiment, through the spraying, filtered and/or dried polyoxometalate with water may be sprayed and thus coated on an inactive carrier.

In an embodiment, in the support material of step (B), the polyoxometalate coating amount calculated by Equation 2 below may be 15 to 50%, 20 to 50%, 20 to 40%, or 20 to 30%. Within this range, the catalyst exhibits superior activity and selectivity.

Coating amount (%)=(Total mass of catalyst precursors/total mass of support material)×100. [Equation 2]

In an embodiment, through the coating of step (B), coating and drying the polyoxometalate on the inactive carrier may be repeated once or more, one to ten times, once to eight times, or five times to eight times. Within this range, the catalyst exhibits superior activity and selectivity.

In an embodiment, in step (C), the drying may be hot air drying.

In an embodiment, the drying may be performed in a container such as a silicon carbide (SiC), alumina, stainless, or metal container, or a container composed of a nonflammable material and having heat transfer characteristics.

In an embodiment, the drying of step (C) may be performed at 100 to 230° C., 110 to 200° C. or 120 to 150° C. for 3 to 10 hours, or 5 to 8 hours.

In an embodiment, the ligand sublimation rate of step (C) may be 1.7% or more, or 1.7 to 4%. Within this range, activity, selectivity and lifespan of the catalyst are greatly enhanced.

In an embodiment, the firing of step (D) may be performed at 350 to 550° C., or 400 to 500° C. for 1 to 10 hours, or 3 to 5 hours.

In an embodiment, in steps (A) to (D), total reduction rates (%) calculated by Equation 3 below may be 30 to 50%, 35 to 45%, or 40 to 45%. Within this range, the catalyst exhibits superior activity and selectivity.

Total weight reduction rate (%)=(Mass of removed material/Mass of all added materials including solvent)×100. [Equation 3]

In an embodiment, in steps (A) to (D), total ligand sublimation rates (%) calculated by Equation 4 below may be 0.1 to 20%, 1 to 10%, or 2 to 5%. Within this range, the catalyst exhibits superior activity and selectivity.

Total ligand sublimation rate (%)=(Mass of removed ligand/Mass of added total materials including solvent)×100. [Equation 4]

In an embodiment, the polyoxometalate catalyst may be a cylinder type, hollow cylinder type or sphere.

In an embodiment, an external diameter of the polyoxometalate catalyst may be 3 to 10 mm, or 5 to 8 mm.

In an embodiment, a ratio (L/D) of the length to the diameter (external diameter) of the cylinder type catalyst may be 1 or less, 0.1 to 1, or 1.0 to 1.3.

In a method of preparing an unsaturated carboxylic acid according to the present invention, partial vapor-phase oxidation to produce unsaturated carboxylic acid from unsaturated aldehyde gas is preformed in a fixed-bed catalyst reactor filled with the polyoxometalate catalyst according to claims 1 at 240 to 450° C. under 0.1 to 10 atm.

In an embodiment, the unsaturated aldehyde may be (meth)acrolein.

In an embodiment, the unsaturated carboxylic acid may be unsaturated fatty acid. In another embodiment, the unsaturated carboxylic acid may be (meth)acrylic acid, etc.

In an embodiment, the fixed-bed catalyst reactor may be a fixed-bed catalyst reactor wherein filling is performed such that occupation volumes of catalysts are decreased.

In an embodiment, the unsaturated aldehyde gas may be input with an unsaturated fatty acid.

In an embodiment, the partial vapor-phase oxidation may be performed at 240 to 370° C. and 0.4 to 3 atm. In another embodiment, the partial vapor-phase oxidation may be performed at 250 to 310° C. and 1 to 3 atm.

In an embodiment, the partial vapor-phase oxidation may be performed in a reactor in which a space velocity of unsaturated aldehyde is 80 to 100 hr-1, the content of oxygen is 20% by volume or less (except for 0% by volume), the content of vapor is 50% by volume or less (except for 0% by volume), and the content of inactive gas is 20 to 80% by volume.

In another embodiment, the partial vapor-phase oxidation may be performed in a reactor to which gas, as a raw material, including a mixture of unsaturated aldehyde, oxygen, vapor and nitrogen is introduced at a space velocity of 500 to 3000 hr-1 (STP).

In an embodiment, the fixed-bed catalyst reactor may be a shell-and-tube heat exchanger.

In an embodiment, the shell-and-tube heat exchanger may be a silicon carbide (SiC), stainless steel or metal container, or a container having heat transfer characteristics.

Now, the present invention will be described in more detail with reference to the following examples. These examples are provided only for illustration of the present invention and should not be construed as limiting the scope and spirit of the present invention.

Example 1

Catalyst 1

While heating and stirring 3000 ml of distilled water at 100° C., 246 g of ammonium tungstate, 1,000 g of ammonium molybdate, 12 g of Niobium(V) oxide were added thereto, thereby preparing solution (1) composed of Mo, A and B among ingredients of Formula 1. Separately, 276 g of ammonium vanadate was dissolved in 1000 ml of distilled water, and then, 300 cc of 10 wt % dilute sulfuric acid and 50 g of zinc were slowly added thereto until a yellow solution was changed to a blue solution, thereby preparing solution (2).

Solutions (1) and (2) were mixed, and then, 570 g of copper nitrate, 99 g of strontium nitrate, 23 g of manganese nitrate and 95 g of ferric nitrate as C and D ingredients of Formula 1 were added thereto, thereby preparing a suspension. pH of the suspension was adjusted to 4 to 5 using dilute sulfuric acid, and then, a homogenizer was operated until slurry-state polyoxometalate having sufficiently increased viscosity was prepared.

Subsequently, the slurry-state polyoxometalate was coated on aluminosilica (Saint Gobain, SA5218), as a sphere carrier, having an external diameter of 4.0 to 8.0 mm by means of a spray nozzle and sufficiently dried at 120° C. Such coating and drying processes were repeated eight times, thereby preparing a support material having a coating amount of 25% by weight.

Subsequently, the support material was fired at 500° C. for five hours or more, thereby preparing a sphere-type polyoxometalate catalyst, final external diameters of which were in turn 4.7 mm 5.4 mm and 7.8 mm which were 0.2 to 0.4 mm larger than those of a carrier. Here, element compositions, except for oxygen, of the generated polyoxometalate catalyst are as follows.

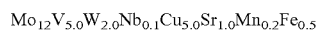

Example 2

Catalyst 2

Experiments were performed in the same manner as in the Example 1, except that the viscosity of a slurry solution was adjusted to 3,000 to 8,000 centipoise (cP) by properly elevating temperature upon operation of a homogenizer and sufficiently dried at 120° C., followed by finely grinding (average particle diameter is 60 to 100 micrometers). Subsequently, a powder along with water, the amount of the water corresponding to 10 to 15% by weight of a sphere carrier (aluminosilica) was sprayed and coated on the sphere carrier (aluminosilica) having an external diameter of 4.0 to 8.0 mm. The coating was performed to a coating amount of 25% by weight and then sufficiently dried until weight change was not exhibited at 120° C. Subsequently, firing was performed in the same manner as in Example 1. As a result, a spherical polyoxometalate catalyst having external diameters of in turn 4.7 mm, 5.4 mm and 7.8 mm which were 0.2 to 0.4 mm larger than those of a carrier was prepared. The compositions of elements, except for oxygen, of generated catalyst ingredients were the same as those of Catalyst 1.

Example 3

Catalyst 3

A polyoxometalate catalyst was prepared in the same manner as in Example 1, except that niobium ethoxide ($Nb_2(OC_2H_5)_{10}$) was used instead of niobium(V) oxide upon preparation of solution (1), vanadium pentoxide ($V_2O_5$) was used instead of ammonium vanadate upon preparation of solution (2), copper acetate ($Cu(CH_3COO)_2 \cdot H_2O$) was used instead of copper nitrate, and pH of the suspension was adjusted to 3 to 4 by means of dilute sulfuric acid. The compositions of elements, except for oxygen, of generated catalyst ingredients were the same as those of Catalyst 1.

Example 4

Catalyst 4

A polyoxometalate catalyst was prepared in the same manner as in Example 1, except that niobium oxalate ($NbC_2O_4$) was used instead of niobium(V) oxide, 137 g of cobalt nitrate was used instead of manganese nitrate, ferric nitrate and copper nitrate, and pH of the suspension was adjusted to pH 3 to 4 by means of dilute sulfuric acid, upon preparation of solution (1). Compositions of elements, except for oxygen, of catalyst ingredients are as follows.

$Mo_{12}V_{5.0}W_{2.0}Nb_{0.1}Sr_{1.0}Co_{1.0}$

Example 5

Catalyst 5

While heating and stiffing 4000 ml of distilled water at 100° C., 369 g of ammonium tungstate, 1,000 g of ammonium molybdate, and 12 g of Niobium(V) oxide were dissolved therein, thereby preparing solution (1) composed of Mo, A and B among ingredients of Formula 1. Separately, 165 g of ammonium vanadate was dissolved in 1000 ml of distilled water, and then, 300 cc of 10 wt % dilute sulfuric acid and 30 g of zinc were slowly added thereto until a yellow solution was changed to a blue solution, thereby preparing solution (2).

To a mixture of solutions (1) and (2), 99 g of strontium nitrate, 68 g of cobalt nitrate and 95 g of ferric nitrate as B, C and D ingredients of Formula 1 were added thereto, thereby preparing a suspension. pH of the suspension was adjusted to 4 to 5 using dilute sulfuric acid, and then, a homogenizer was operated until slurry-state polyoxometalate having sufficiently increased viscosity was prepared.

Subsequently, polyoxometalate sediments including a supernatant were filtered by means of a filter press. After filtering, a remaining cake was sufficiently dried at 120° C. Subsequently, a polyoxometalate catalyst was prepared in the same manner as in Example 2. Compositions of elements, except for oxygen, of generated catalyst ingredients are as follows.

$Mo_{12}V_{3.0}W_{3.0}Nb_{0.1}Sr_{1.0}Co_{0.5}Fe_{0.5}$

Example 6

Catalyst 6

A polyoxometalate catalyst was prepared in the same manner as in Example 1, except that solution (1) was prepared according to Example 4, 82.82 g of ammonium vanadate was dissolved in the solution (1) including 1000 ml of water, an aqueous ammonium vanadate solution treated with 200 cc of 10 wt % dilute sulfuric acid and 15 g of zinc was added thereto, 549 g of nickel nitrate was used instead of strontium nitrate and cobalt nitrate, and pH of a suspension was adjusted to 4 to 5 by means of dilute sulfuric acid. Compositions of elements, except for oxygen, of generated catalyst ingredients are as follows.

$Mo_{12}V_{1.5}W_{2.0}Nb_{0.1}Ni_{4.0}$

Comparative Example 1

Catalyst 7

While heating and stiffing 4000 ml of distilled water was heated and stirred at 100° C., 246 g of ammonium tungstate, 1,000 g of ammonium molybdate and 276 g of ammonium vanadate were dissolved therein, thereby preparing solution (1) composed of Mo, A and B ingredients of Formula 1.

To solution (1), 570 g of copper nitrate, 99 g of strontium nitrate, 12 g of Niobium(V) oxide, 23 g of manganese nitrate and 95 g of ferric nitrate as B, C and D ingredients of Formula 1 were added, thereby preparing a suspension. A homogenizer was operated until the suspension was prepared into polyoxometalate having sufficiently increased viscosity.

Subsequently, slurry-state polyoxometalate was coated on a sphere carrier (aluminosilica) having an external diameter of 4.0 mm to 8.0 mm by means of a spray nozzle and sufficiently dried at 120° C. These coating and drying processes were repeated several times, thereby preparing a support material having a coating amount of 25 wt %. Hereinafter, a polyoxometalate catalyst was prepared in the same manner as in Example 1. Compositions of elements, except for oxygen, of generated catalyst ingredients are as follows.

$Mo_{12}V_{5.0}W_{2.0}Nb_{0.1}Cu_{5.0}Sr_{1.0}Mn_{0.2}Fe_{0.5}$

Comparative Example 2

Catalyst 8

A polyoxometalate catalyst was prepared in the same manner as in Example 5, except for reduction methods of cobalt nitrate and ammonium vanadate. Compositions of elements, except for oxygen, of generated catalyst ingredients are as follows.

$$Mo_{12}V_{3.0}W_{3.0}Nb_{0.1}Sr_{1.0}Fe_{0.5}$$

Test Example

Characteristics of polyoxometalate catalysts prepared according to Examples 1 to 6 and Comparative Examples 1 to 2 was measured according to methods below. Results are summarized in Table 1 below.

Ratios of $V^{4+}$ and $V^{5+}$: Measured using prepared catalysts by means of XPS (ESCA) (Device name: X-ray photoelectron spectrum analyzer, model name: UK-Multilab 2000, manufacturer: thermos VG).

Ligand sublimation rate: The masses of sublimated ligands were measured and calculated according to Equation 1 below.

Ligand sublimation rate (%)=(Mass of sublimated ligand/mass of ligand before sublimation)×100. [Equation 1]

Viscosity (cP): Brookfield viscometer, spindle #63 and RPM 2 were used, and measurements were performed at room temperature (resistance: 5 to 6%).

<Catalytic Activity Test>

Each of catalysts obtained according to Examples 1 to 6 and Comparative Examples 1 to 2 was subject to partial vapor-phase oxidation by introducing aldehyde with a mix gas composed of oxygen, vapor and inactive gas, at a space velocity of 100 hr-1, to a stainless reactor filled with a fixed bed at 240 to 310° C. under a reaction pressure of 1 to 3 atm. During reaction progress, a transition rate, selectivity and yield of a reactant (acrolein) were respectively calculated according to Equations 2 to 4 below. Results are summarized in Table 1 below.

Acrolein transition rate (%)=[Mole number of reacted acrolein/mole number of supplied acrolein]×100. [Equation 5]

Acrolein selectivity (%)=[Mole number of generated acrylic acid/mole number of reacted acrolein]×100. [Equation 6]

Yield (%)=[Mole number of generated acrylic acid/mole number of supplied acrolein]×100. [Equation 7]

As shown in Table 1, it can be confirmed that, in the cases of the polyoxometalate catalysts in which an oxidation number of vanadium is controlled according to the present invention (Examples 1 to 6), all of transition rate, selectivity and yield are superior, compared to conventional technology or the cases in which an oxidation number of vanadium is not adjusted (Comparative Examples 1 and 2).

In addition, it can be confirmed that ligand sublimation rates, pH of the suspensions, etc. somewhat affect catalyst activity, selectivity and yield.

Furthermore, it can be confirmed that, in the cases of the polyoxometalate catalysts according to the present invention (Examples 1 to 6), operation may be performed in a wider temperature range of 250 to 310° C. for a long time unlike conventional technology in which operation is performed at a reaction temperature of 270 to 310° C.

What is claimed is:

1. A polyoxometalate catalyst comprising a metal oxide represented by Formula 1 below:

$$Mo_aA_bV_cB_dC_eD_fO_g \quad \text{[Formula 1]}$$

wherein A is at least one element selected from W and Cr, B is at least one element selected from the group consisting of P, As, B, Sb, Ce, Pb, Mn, Nb and Te, C is at least one element selected from the group consisting of Si, Al, Zr, Rh, Cu, Ni, Ti, Ag, Fe, Co and Sn, D is at least one element selected from the group consisting of Na, K, Li, Rb, Cs, Ta, Ca, Mg, Sr and Ba, and a, b, c, d, e, f and g denote an atomic ratio of each element, but, when a=12, b is 0.01 to 15, c is 0.01 to 15, d is 0 to 20, e is 0 to 20, f is 0 to 20, and g is determined according to an oxidation state of each of the ingredients, wherein, in the vanadium (V), a mole ratio of $V^{4+}$ relative to a sum of $V^{4+}$ and $V^{5+}$ is 0.47 to 1.

2. The polyoxometalate catalyst according to claim 1, wherein each of d, e and f is 0.01 to 20.

3. The polyoxometalate catalyst according to claim 1, wherein a mole ratio of V to A (V/A) is 0.01 to 10.

4. The polyoxometalate catalyst according to claim 1, wherein the polyoxometalate catalyst comprises an inactive carrier as a support of the metal oxide.

5. The polyoxometalate catalyst according to claim 4, wherein a coating amount of the metal oxide coated on the inactive carrier is 30 to 80% by weight.

6. The polyoxometalate catalyst according to claim 1, wherein the polyoxometalate catalyst is a partial vapor-phase oxidation catalyst generating carboxylic acid from unsaturated aldehyde.

TABLE 1

| Classification | Ligand sublimation rate (wt %) | Mole ratio of V/W | pH of reaction solution | Ratio of $V^{4+}/(V^{4+} + V^{5+})$ | Acrolein transition rate (%) | Acrolein selectivity (%) | Acrylic acid yield (%) |
|---|---|---|---|---|---|---|---|
| Example 1 | 2.3 | 2.5 | 4~5 | 0.54 | 98.70 | 96.10 | 94.84 |
| Example 2 | 3.1 | 2.5 | 4~5 | 0.56 | 97.40 | 96.57 | 94.05 |
| Example 3 | 3.8 | 2.5 | 3~4 | 0.72 | 99.57 | 96.50 | 96.08 |
| Example 4 | 3.6 | 2.5 | 3~4 | 0.63 | 97.80 | 95.80 | 93.70 |
| Example 5 | 1.8 | 1 | 4~5 | 0.65 | 98.30 | 94.80 | 93.18 |
| Example 6 | 2.1 | 0.75 | 4~5 | 0.52 | 98.87 | 96.18 | 95.09 |
| Comparative Example 1 | 1.3 | 2.5 | 6.7 | 0.46 | 97.55 | 95.40 | 93.06 |
| Comparative Example 2 | 1.6 | 1 | 6.7 | 0.41 | 97.78 | 95.00 | 92.89 |

7. A method of preparing a polyoxometalate catalyst, the method comprising: A) preparing a suspension including metal precursors in order to produce a metal oxide represented by Formula 1 and, as needed, adjusting pH to 0 to 7.5 through addition of acid, and then forming polyoxometalate by increasing viscosity using a homogenizer; B) preparing a support material by coating an inactive carrier with 20 to 50% by weight of the polyoxometalate; C) obtaining a support material having a ligand sublimation rate of 0% or more as calculated according to Equation 1 below by drying the support material; and D) obtaining a polyoxometalate catalyst by firing the dried support material:

Ligand sublimation rate (%)=(Mass of sublimated ligand/mass of ligand before sublimation)×100.  [Equation 1]

8. The method according to claim 7, wherein a viscosity of the polyoxometalate of step (A) is 5,000 to 20,000 cP.

9. The method according to claim 7, wherein the polyoxometalate of step (A) is ground after drying, or filtrating and drying.

10. The method according to claim 7, wherein the coating of step (B) is performed by spraying the polyoxometalate, or the polyoxometalate with water to the inactive carrier.

11. The method according to claim 7, wherein the suspension of step (A) is prepared by inputting an aqueous vanadium solution treated with acid and metal to a suspension comprising all or a portion of metal precursors except for a vanadium precursor.

12. The method according to claim 7, wherein a ligand of the metal precursor is one or more selected from $-NH_4$, $-NH_2$, $-NOx$ (x being an integer of 1 to 3), $-Cl$, $-F$, $-N$, $-OH$, $-SOx$ (x is an integer of 3 to 4), $-CO$, $-COO$, $-SCN$, $-CN$, $-NCS$, $-ONO$, $-NC$, $-C_nH_mO_x$ (n being an integer of 1 to 20, m being an integer of 1 to 40, and x being an integer of 1 to 10) and $C_1$ to $C_{20}$ alkoxide.

13. The method according to claim 7, wherein, in step (A), a concentration of the suspension is 25 to 45% by weight.

14. The method according to claim 7, wherein, in step (C), the drying is hot air drying.

15. The method according to claim 7, wherein the coating of step (B) is performed by repeatedly coating and drying the polyoxometalate on the inactive carrier once or more.

16. The method according to claim 7, wherein the drying of step (C) is performed at 100 to 230° C.

17. The method according to claim 7, wherein, in step (A), the polyoxometalate is formed by increasing a viscosity of the suspension by means of a homogenizer at 25 to 50° C.

18. The method according to claim 7, wherein the firing of step (D) is performed at 350 to 550° C. for 1 to 10 hr.

19. A method of preparing unsaturated carboxylic acid wherein partial vapor-phase oxidation to produce unsaturated carboxylic acid from unsaturated aldehyde gas is preformed in a fixed-bed catalyst reactor filled with the polyoxometalate catalyst according to claims 1 at 240 to 450° C. under 0.1 to 10 atm.

20. The method according to claim 19, wherein the fixed-bed catalyst reactor is a shell-and-tube heat exchanger.

* * * * *